US00PP24403P2

(12) United States Plant Patent
Hooijman

(10) Patent No.: US PP24,403 P2
(45) Date of Patent: Apr. 29, 2014

(54) ROSE PLANT NAMED 'ESM R044'

(50) Latin Name: *Rosa hybrida*
Varietal Denomination: ESM R044

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 60 days.

(21) Appl. No.: 13/507,629

(22) Filed: Jul. 13, 2012

(51) Int. Cl.
*A01H 5/00* (2006.01)

(52) U.S. Cl.
USPC ..... Plt./130

(58) Field of Classification Search
USPC ..... Plt./130
See application file for complete search history.

*Primary Examiner* — Annette Para
(74) *Attorney, Agent, or Firm* — C. A. Whealy

(57) ABSTRACT

A new and distinct cultivar of Rose plant named 'ESM R044', characterized by its upright, long and strong flowering stems; vigorous growth habit and high productivity; light red purple-colored flowers that are typically grown as single stems; excellent postproduction longevity; and relative tolerance to Downy Mildew and *Botrytis*.

1 Drawing Sheet

Botanical designation: *Rosa hybrida*.
Cultivar denomination: 'ESM R044'.

BACKGROUND OF THE INVENTION

The present Invention relates to a new and distinct cultivar of Rose plant, botanically known as *Rosa hybrida*, which is commercially produced as a cut flower Rose plant and hereinafter referred to by the name 'ESM R044'.

The new Rose plant is a product of a planned breeding program conducted by the Inventor in El Quinche, Pichincha, Ecuador. The objective of the breeding program was to develop new cut flower Rose varieties with unique and attractive flowers and excellent postproduction longevity.

The new Rose plant originated from a cross-pollination made by the Inventor in June, 2006 of a proprietary Rose selection identified as Line 370, not patented, as the female, or seed, parent with a proprietary Rose selection identified as Line 347, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in November, 2007.

Asexual reproduction of the new Rose plant by bud grafting in El Quinche, Pichincha, Ecuador since March, 2008 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype of the new Rose plant may vary somewhat with variations in environmental conditions such as temperature and light intensity, without however, any variance in genotype.

The following traits have been repeatedly observed and are determined to be the unique characteristics of 'ESM R044'.

These characteristics in combination distinguish 'ESM R044' as a new and distinct Rose plant:

1. Upright, long and strong flowering stems.
2. Vigorous growth habit and high productivity.
3. Light red purple-colored flowers that are typically grown as single stems.
4. Excellent postproduction longevity.
5. Relative tolerance to Downy Mildew and *Botrytis*.

Plants of the new Rose differ from plants of the female parent selection in the following characteristics:

1. Plants of the new Rose are larger than plants of female parent selection.
2. Plants of the new Rose have larger flowers than plants of female parent selection.
3. Plants of the new Rose and the female parent selection differ in flower color as plants of the female parent selection have fuchsia-colored flowers.

Plants of the new Rose differ from plants of the male parent selection in the following characteristics:

1. Plants of the new Rose are more vigorous than plants of the male parent selection.
2. Plants of the new Rose have slightly smaller flowers than plants of male parent selection.
3. Plants of the new Rose and the male parent selection differ in flower color as plants of the male parent selection have hot pink-colored flowers.

Plants of the new Rose can be compared to plants of Rose 'Hot Party', not patented. In side-by-side comparisons conducted in El Quinche, Pichincha, Ecuador, plants of the new Rose differed from plants of 'Hot Party' in the following characteristics:

1. Plants of the new Rose were more vigorous than plants of 'Hot Party'.
2. Plants of the new Rose had smaller leaflets than plants of 'Hot Party'.
3. Plants of the new Rose had larger flowers than plants of 'Hot Party'.
4. Plants of the new Rose flowered later than plants of 'Hot Party'.

5. Plants of the new Rose and 'Hot Party' differed slightly in flower color.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of typical flowering stem of 'ESM R044'.

The photographs at the lower left and upper right of the sheet are close-up views of typical flowers of 'ESM R044'.

The photographs at the bottom right of the sheet are close-up views of the upper and lower surfaces of typical leaves of 'ESM R044'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched about 13 to 14 weeks after planting. Plants were 69 weeks old when the photographs and detailed description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R044'.

Parentage:

*Female, or seed, parent.*—Proprietary seedling selection of *Rosa hybrida* identified Line 370, not patented.

*Male, or pollen, parent.*—Proprietary seedling selection of *Rosa hybrida* identified Line 347, not patented.

Propagation:

*Type.*—By bud grafting.

*Time to initiate roots.*—About seven to ten days at 26° C. to 30° C.

*Time to produce a rooted young plant.*—About four to five weeks at 22° C. to 26° C.

*Root description.*—Fibrous, medium to thick; close to 200C in color.

*Rooting habit.*—Freely branching; dense.

Plant description:

*Plant and growth habit.*—Perennial shrub; upright, long and strong flowering stems; typically grown as a single-stem cut flower; vigorous growth habit.

*Branching habit.*—Freely basal branching habit; highly productive with about 14.4 flowering stems developing per plant per year.

*Plant height.*—About 140 cm.

*Plant width* (*spread*).—About 65 cm.

*Lateral branches* (*peduncles*).—Length: About 75 cm. Diameter: About 8 mm. Internode length: About 5.1 cm. Texture: Smooth, glabrous; older stems, woody. Color: Close to 146A tinted with close to N199A. Thorns: Density: Medium density. Shape: Triangular with sharp acuminate apices; slightly incurved. Height: About 8 mm. Length, at base: About 1.4 cm. Color, immature: Close to 199A tinted with close to 183A. Color, mature: Between N199A and 200C.

Foliage description:

*Arrangement.*—Alternate; compound with typically five to seven leaflets per leaf.

*Leaf length.*—About 16.8 cm.

*Leaf width.*—About 11.7 cm.

*Terminal leaflet length.*—About 6.4 cm.

*Terminal leaflet width.*—About 4.8 cm.

*Lateral leaflet length.*—About 5.3 cm.

*Lateral leaflet width.*—About 4.1 cm.

*Leaflet shape.*—Ovate.

*Leaflet apex.*—Acute.

*Leaflet base.*—Attenuate.

*Leaflet margin.*—Serrate.

*Leaflet texture, upper and lower surfaces.*—Smooth, glabrous; coriaceous.

*Leaflet venation pattern.*—Pinnate.

*Leaflet color.*—Developing leaflets, upper surface: Close to 139A; towards the margins, close to 187C. Developing leaflets, lower surface: Close to 147B tinted with close to N199A. Fully expanded leaflets, upper surface: Close to 147A; venation, close to 146C. Fully expanded leaflets, lower surface: Close to 147B; venation, close to 146D.

*Petioles, leaves.*—Length: About 9 mm. Diameter: About 2 mm. Texture, upper surface: Prickly. Texture, lower surface: Smooth, glabrous. Color, upper surface: Between 144A and 146A. Color, lower surface: Close to 146A.

*Petioles, leaflets.*—Length: About 2.1 cm. Diameter: About 1 mm. Texture, upper surface: Prickly. Texture, lower surface: Smooth, glabrous. Color, upper surface: Close to 146A. Color, lower surface: Between 144A and 146A.

*Stipules.*—Arrangement and appearance: Two, adnate to the petiole, leafy in appearance. Length: About 2.2 cm. Width: About 2 mm. Shape: Roughly deltoid. Apex: Acuminate. Base: Truncate. Margin: Serrate; glandular. Texture, upper and lower surfaces: Smooth, glabrous; membranous. Venation pattern: Pinnate. Color, upper surface: Close to 137B. Color, lower surface: Close to 137C.

Flower description:

*Flower type and flowering habit.*—Symmetrical rosette flowers; flowers typically grown as single stems; flowers face upright.

*Flowering season.*—Plants of the new Rose flower year-round under greenhouse conditions; early flowering habit, plants begin flowering about 68 days after pinching; in the garden, optimal flowering from spring through autumn; flowering intermittent.

*Flower diameter.*—About 13 cm.

*Flower depth* (*height*).—About 6 cm.

*Flower longevity on plant.*—About 26 days; flowers persistent.

*Flower longevity as a cut flower.*—Excellent postproduction longevity, flowers last about twelve days.

*Fragrance.*—Very faintly fragrant, pleasant.

*Flower buds.*—Shape: Ovoid. Length: About 6 cm. Diameter: About 4 cm. Color: Between 143A and 144A.

*Petals.*—Quantity: About 40 per flower; petals imbricate. Length: About 6.7 cm. Width: About 7.6 cm.

Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Between N57D and 61C; towards the base, close to 160B. When opening, lower surface: Close to N66B; towards the base, close to 160D. Fully opened, upper surface: Close to 61C; center and towards the base, close to 64D. Fully opened, lower surface: Close to 57C.

*Petaloids.*—Quantity: About four; petaloids whorled. Length: Variable. Width: Variable. Shape: Irregularly shaped. Apex: Blunt to shortly acute. Base: Obtuse. Margin: Entire or uneven. Texture, upper and lower surfaces: Smooth, glabrous; papery to coriaceous. Color: When opening and fully opened, upper surface: Between 63A and 59D; center and towards the base, close to 152D. When opening and fully opened, lower surface: Close to N57B to N57D; towards the base, close to 157A.

*Sepals.*—Quantity per flower: Typically five in a single whorl. Length: About 4.8 cm. Width: About 1.4 cm. Shape: Roughly deltoid. Apex: Tapered. Base: Truncate. Margin: Entire; glandular and ciliate. Texture, upper and lower surfaces: Leathery. Color: When opening, upper surface: Close to 146C. When opening, lower surface: Close to 144A. Fully opened, upper surface: Close to 146B to 146C. Fully opened, lower surface: Close to 144A.

*Reproductive organs.*—Stamens: Quantity: About 180 per flower. Anther length: About 3 mm. Anther shape: Reniform. Anther color: Close to 162A and 54C. Filament color: Close to 160B and 51B. Pollen amount: Moderate. Pollen color: Close to N167A. Pistils: Quantity: About 249 per flower. Pistil length: About 1.4 cm. Stigma shape: Broadly reniform. Stigma color: Close to 161A. Style length: About 9 mm. Style color: Close to 161D. Receptacle height: About 1.5 cm. Receptacle diameter: About 1.2 cm. Receptacle shape: Cup-shaped. Receptacle texture: Smooth, glabrous. Receptacle color: Close to 144A. Fruits: Quantity per flower: One. Length: About 3.2 cm. Diameter: About 2.3 cm. Texture: Smooth, glabrous. Color: Close to N163B. Seeds: Quantity per fruit: About 12.7. Length: About 8 mm. Diameter: About 5 mm. Texture: Smooth, glabrous. Color: Close to 159D tinted with close to N144A.

Pathogen & pest resistance: Plants of the new Rose have been observed to be relatively tolerant to Downy Mildew and *Botrytis*. Plants of the new Rose have not been observed to be resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R044' as illustrated and described.

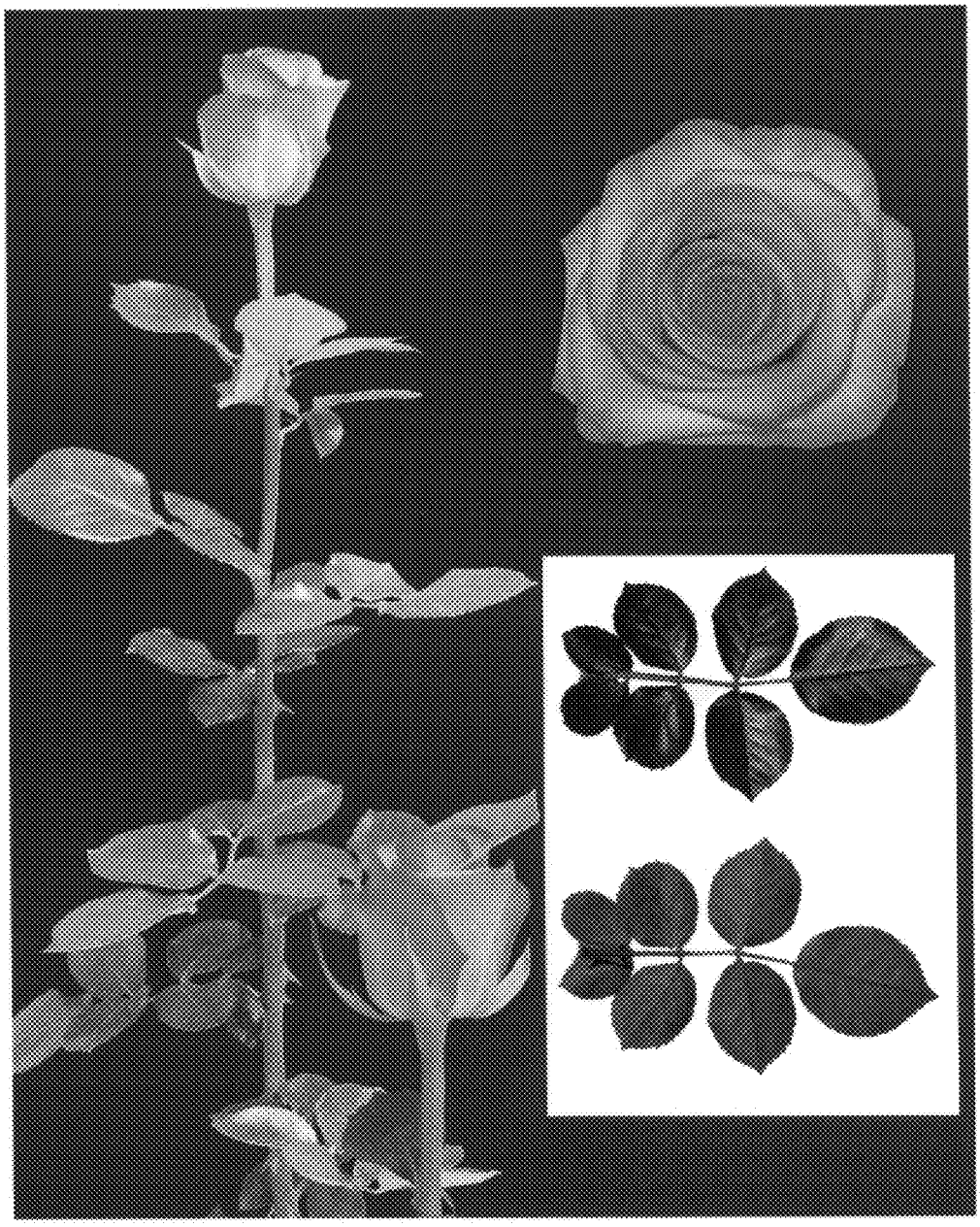

* * * * *